United States Patent
Sevenster et al.

(10) Patent No.: US 10,037,407 B2
(45) Date of Patent: Jul. 31, 2018

(54) STRUCTURED FINDING OBJECTS FOR INTEGRATION OF THIRD PARTY APPLICATIONS IN THE IMAGE INTERPRETATION WORKFLOW

(71) Applicant: KONINKLIJKE PHILIPS N.V., Eindhoven (NL)

(72) Inventors: Merlijn Sevenster, Chicago, IL (US); Gabriel Ryan Mankovich, Boston, MA (US); Ranjith Naveen Tellis, Cambridge, MA (US); Ehsan Dehghan Marvast, New York, NY (US); Yuechen Qian, Lexington, MA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/356,774

(22) Filed: Nov. 21, 2016

(65) Prior Publication Data

US 2017/0154156 A1    Jun. 1, 2017

Related U.S. Application Data

(60) Provisional application No. 62/258,750, filed on Nov. 23, 2015.

(51) Int. Cl.
*G06Q 50/24* (2012.01)
*G06F 19/00* (2018.01)
(Continued)

(52) U.S. Cl.
CPC .......... *G06F 19/321* (2013.01); *G06F 17/241* (2013.01); *G06F 17/243* (2013.01);
(Continued)

(58) Field of Classification Search
None
See application file for complete search history.

(56) References Cited

U.S. PATENT DOCUMENTS

2002/0194219 A1\* 12/2002 Bradley ................ G06F 17/243
715/223
2005/0222250 A1\* 10/2005 Rezvani ................ A61K 31/12
514/461
(Continued)

FOREIGN PATENT DOCUMENTS

WO    2013160382 A1    10/2013

OTHER PUBLICATIONS

Rubin, D.L. et al., "Annotation and Image markup: Accessing and Interoperating with the Semantic Content in Medical Imaging". Jan./Feb. 2009, IEEE Computer Society.
(Continued)

*Primary Examiner* — Mohammed-Ibrahim Zuberi

(57) ABSTRACT

A radiology workstation (16) includes a display device (25) and at least one user input device (20, 22, 24). A server computer (10) is programmed to operate with the radiology workstation to perform the radiology reading task (14) including a radiology reading support method comprising: receiving user input identifying a radiological finding; retrieving a structured finding object (SFO) template for the radiological finding; displaying an SFO annotation graphical user interface (GUI) dialog (40) having annotation data entry fields for annotating the retrieved SFO template; building an SFO (60) representing the radiological finding by annotating the SFO template via the SFO GUI dialog; and generating natural language text describing the radiological finding from the SFO. Application program interface (API) action rules (54) may be applied to determine whether the
(Continued)

SFO being built satisfies any API action rule, and if so a corresponding application program is invoked.

20 Claims, 2 Drawing Sheets

(51) Int. Cl.
    *G06F 17/24*     (2006.01)
    *G06F 17/28*     (2006.01)
    *G06T 7/00*     (2017.01)
    *G16H 40/63*     (2018.01)
    *G16H 10/60*     (2018.01)
    *G16H 15/00*     (2018.01)
    *G06F 3/0481*     (2013.01)

(52) U.S. Cl.
    CPC ............ *G06F 17/248* (2013.01); *G06F 17/28* (2013.01); *G06T 7/0012* (2013.01); *G16H 10/60* (2018.01); *G16H 15/00* (2018.01); *G16H 40/63* (2018.01); *G06F 3/0481* (2013.01)

(56) References Cited

U.S. PATENT DOCUMENTS

| | | | |
|---|---|---|---|
| 2012/0035963 A1* | 2/2012 | Qian | G06F 19/3487 705/3 |
| 2013/0094732 A1* | 4/2013 | Chabanas | G06K 9/6205 382/128 |
| 2013/0339345 A1* | 12/2013 | Soto Matamala | G06F 17/3089 707/722 |
| 2014/0010421 A1 | 1/2014 | Colaco et al. | |
| 2015/0324523 A1* | 11/2015 | Parthasarathy | G06F 19/322 705/2 |
| 2017/0154156 A1* | 6/2017 | Sevenster | G06F 19/321 |
| 2017/0220860 A1* | 8/2017 | Van Hoe | G06F 17/246 |

OTHER PUBLICATIONS

Application programming interface—Wkipedia, the free encyclopedia.

\* cited by examiner

STRUCTURED FINDING OBJECTS FOR INTEGRATION OF THIRD PARTY APPLICATIONS IN THE IMAGE INTERPRETATION WORKFLOW

FIELD

The following relates generally to the radiology arts, radiology reading arts, radiology workstation arts, radiology workstation user interfacing arts, and related arts.

BACKGROUND

Radiology is a complex process involving several interacting medical professionals. In a typical sequence, a patient's physician orders a radiology examination. A radiology technician operates the imaging system, such as a magnetic resonance imaging (MRI) system, a computed tomography (CT) imaging system, a positron emission tomography (PET) imaging system, or so forth, or a combination of imaging system (e.g. PET/CT) to acquire images of an anatomical region of the patient in accordance with the physician's order. These images are stored in a Picture Archiving and Communication System (PACS), and are later viewed, or "read", by a radiologist, typically using a dedicated radiology workstation executing a radiology reading environment. The main deliverable of the radiology reading is a radiology report, which is generally a narrative document divided in several sections that detail, respectively, the patient's clinical history, the main image findings and conclusions. Workflow may be made more efficient through the use of improvements such as speech recognition for dictating the radiology report, and through the use of standardized reporting templates such as RSNA templates in conjunction with standardized vocabulary.

Radiology reading is a complex task, whose results can be critical to providing a timely and accurate medical diagnosis and consequent treatment regimen. Various support tools are available for assisting the radiologist, such as medical literature, patient data available in the Electronic Medical Record (EMR), treatment guidelines for various conditions, computer-aided diagnostic (CADx) systems, and past radiology examinations of the patient which may be available in the PACS. These tools are typically implemented as third party resources that are separate from the radiology reading environment, although they usually can be accessed at the radiologist's initiative from the radiology workstation via the hospital electronic data network.

Radiological imaging is used in the diagnosis and assessment of a wide range of medical conditions ranging from relatively simple bone fractures to complex oncology staging and tumor grading tasks. In many medical institutions, radiology is a high throughput department in which the radiologist is expected to perform many reading tasks per work shift. For example, a typical radiology department may expect the radiologist to perform an x-ray or ultrasound reading in a time frame of two minutes or less, while a more complex reading task such as a multi-slice CT or MRI may be expected to be performed in about five to seven minutes. Under these time constraints, the radiologist may find it difficult to recognize and make use of available tools such as the EMR, past radiology examinations stored in the PACS, and various CADx or electronic treatment guideline resources. Operating under tight time constraints also increases the possibility that the radiologist may fail to provide sufficient support for a radiology finding in the written radiology report, or may fail to make and record appropriate secondary findings.

Improvements disclosed herein address the foregoing and other disadvantages of existing radiology reading systems, methods, and the like.

BRIEF SUMMARY

In accordance with one illustrative example, a radiology reading device comprises a server computer programmed to operate with a radiology workstation to perform a radiology reading task including performing an SFO-based radiology reading support method including: receiving user input identifying a radiological finding via at least one user input device of the radiology workstation; retrieving from a data storage a structured finding object (SFO) template comprising a structured data object configured to represent the identified radiological finding; displaying an SFO annotation graphical user interface (GUI) dialog on a display device of the radiology workstation with annotation data entry fields for annotating the retrieved SFO template; building an SFO representing the identified radiological finding by annotating the retrieved SFO template at least in part with information received via the at least one user input device interacting with the SFO GUI dialog displayed on the display device of the radiology workstation; and generating natural language text describing the identified radiological finding from the SFO representing the identified radiological finding.

In accordance with another illustrative example, a radiology reading system comprises a data storage storing structured finding object (SFO) templates. Each SFO template is a structured data object configured to represent a radiological finding. A radiology workstation includes a display device and at least one user input device. The radiology reading system further includes a radiology reading device comprising a server computer as set forth in the immediately preceding paragraph programmed to operate with the radiology workstation to perform the radiology reading task including performing the SFO-based radiology reading support method.

In accordance with another illustrative example, a non-transitory storage medium is disclosed which stores instructions readable and executable by an electronic device to perform a radiology reading support method in support of a radiology reading task also being performed on the electronic device operating with a radiology workstation. The radiology reading support method comprises: receiving user input identifying a radiological finding via at least one user input device of the radiology workstation; retrieving from a data storage a structured finding object (SFO) template configured to represent the identified radiological finding at least by defining <key, value> pairs in which the key denotes a dimension of the SFO representing information supporting or characterizing the radiological finding and the value denotes a value for the dimension; displaying an SFO annotation graphical user interface (GUI) dialog on a display device of the radiology workstation, the SFO GUI dialog having annotation data entry fields for entering values for dimensions of the SFO template; building an SFO representing the identified radiological finding at least in part by receiving values for dimensions of the SFO template using the at least one user input device of the radiology workstation interacting with the displayed SFO GUI dialog; and generating natural language text describing the identified radiological finding from the SFO representing the identified radiological finding.

One advantage resides in organizing the radiology reading process around structured finding objects in order to facilitate collection and recordation of appropriate support for radiology findings, and to trigger secondary findings and appropriate use of third party tools.

Another advantage resides in providing a more effective and efficient radiology workstation user interface.

Further advantages of the present invention will be appreciated to those of ordinary skill in the art upon reading and understand the following detailed description. It will be appreciated that a given embodiment may provide none, one, two, or more of these advantages.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
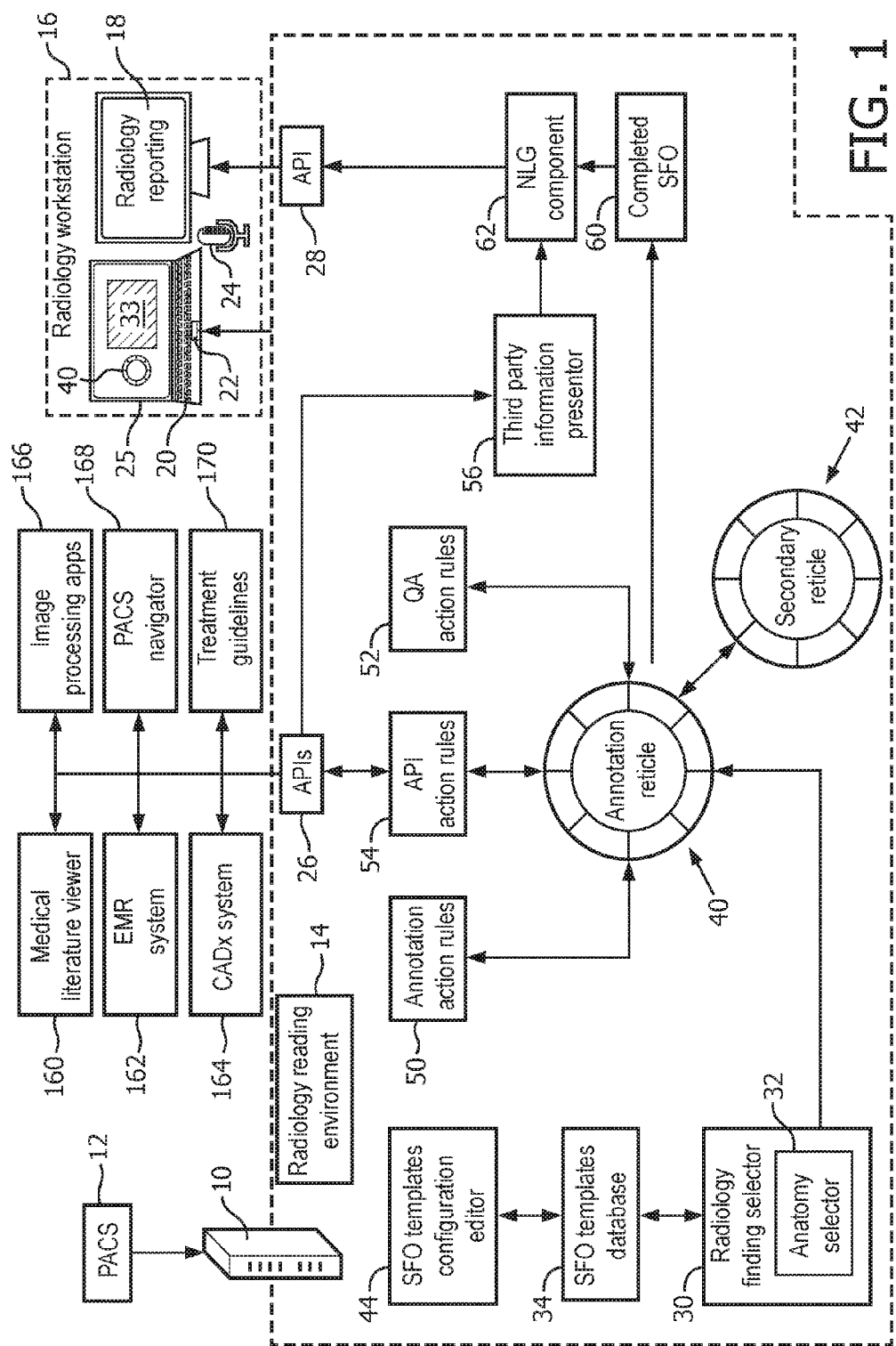
FIG. 1 diagrammatically illustrates a radiology reading device supported by or incorporating a structured finding object (SFO)-based tool for facilitating collection and recordation of support for or characterization of radiological findings, triggering secondary findings, and interfacing with third party tools.

Disclosed radiology reading devices and methods utilize the concept of a structured finding object (SFO), which is a digital entity, preferably codified in a radiological ontology such as RadLex (promulgated by the Radiological Society of North America, RSNA) or Systematized Nomenclature of Medicine—Clinical Terms (SnoMed CT, promulgated by the College of American Pathologists, CAP). The SFO at least partially characterizes an image finding in a structured format using syntax such as Annotation Imaging Mark-up (AIM), which is a radiology domain-specific XML syntax. In some suitable embodiments, an SFO is represented by dimensions each codified using a <key, value> pair where "key" identifies the dimension and "value" is the value of the dimension for the radiological finding in the current reading task. Dimensions are typically typed, and the value for a given dimension may itself be a complex (e.g. hierarchical) data structure. By way of non-limiting illustration, some possible SFO dimensions are as follows. A "diagnosis" dimension may assume a string value from a set of possible diagnoses chosen from the radiology ontology such as "lesion", "nodule", "cyst", "metastatic lesion", "tumor" or so forth, and optionally having additional parameters such as a likelihood or probability value in the range [0,1] or having discrete string values such as "likely", "unlikely", or "presumably". A "spatial" dimension may have a value comprising an ordered triplet of integers or real numbers representing the size in the X, Y and Z directions of a finding (e.g. tumor). The "spatial" dimension may optionally also assume a special value such as "absent" or the special triplet "0,0,0" for annotating a negative finding, e.g. not finding a tumor at all. Additionally or alternatively, a qualitative "size" dimension may be provided, e.g. assuming qualitative values such as "large" or "small". An "anatomy/body part" dimension specifies an anatomical region and may assume string values from the ontology such as "kidney", "left lung", "liver", or so forth. A "sub-location" dimension may further localize the anatomy, e.g. assuming values such as "renal cortex", "left lower lobe", "liver segment 1", or so forth. The set of allowable values for the "sub-location" dimension depends upon the "anatomy/body part" dimension. A "temporal" dimension may assume values such as "stable", "interval increase in size", or so forth. To assign a value for the "temporal" dimension the radiologist may need to refer back to a past radiology examination of the patient, e.g. to assess how the tumor size has changed since that last examination. A "plurality" dimension may assume values such as "one", "multiple", "various", or so forth, and is for example used to specify the number of nodules observed in the image. Additional or other dimensions may be appropriate for a given type of finding, such as an "additional diagnostic" dimension which may assume a value such as "with calcifications" to further characterize a tumor. These are merely non-limiting illustrative dimensions for an SFO, and a SFO of a given type may have additional or other dimensions.

In general, the SFO-based tool disclosed herein initially provides the radiologist with an SFO "template" which is the SFO data structure with dimensions appropriate for the particular finding being reported but with the values of those dimensions (at least mostly) blank. More generally, an SFO template is a structured data object configured to represent a radiological finding, for example by defining <key, value> pairs in which the key denotes a dimension of the SFO representing information supporting or characterizing the radiological finding and the value denotes a value for the dimension. Starting with the SFO template, the radiologist fills in values for dimensions of the SFO via an SFO annotation graphical user interface (GUI) dialog displayed on the radiology workstation (or in some cases, one or more values may be assigned automatically by the SFO-based tool itself or may be assigned by a third party tool invoked by the SFO-based tool) in order to provide documentary support for, or more precise characterization of, the finding. This process of entering values for dimensions of the SFO is referred to herein as "annotation" of the SFO. Completion of SFO annotation results in a completed SFO in which many, and in some cases most or all, dimensions of the SFO are filled with values. In general, a different SFO template is provided for each distinct type of radiological finding. As annotation proceeds, the SFO-based tool monitors the SFO to determine whether any action rule of a set of action rules is met. Action rules may, for example, trigger annotation process modifications such as adding dimensions to the SFO, suggesting values for existing dimensions, or opening a (secondary) SFO annotation GUI dialog. Other action rules may trigger invocation of a third party tool (i.e. application) via a suitable application program interface (API) of the SFO-based tool. Still other action rules may trigger quality control actions, for example triggering display of a notification bubble or window informing the radiologist of an inconsistency between two related dimensions (e.g. a quantitative "spatial" dimension value that indicates a large tumor while the qualitative "size" dimension is set to a "small" value) or identifying missing data (e.g. data that should be provided to adequately support or characterize the finding). This approach leverages the structured nature of the SFO to automatically trigger actions based on the state of the finding being recorded by the radiologist. The completed SFO, along with any information generated by third party applications triggered by action rules during the annotation, serve as inputs to a natural language generation (NLG) component that converts the SFO and any additional information on the finding to natural language text for inclusion in the radiology report.

With reference now to FIG. 1, an illustrative radiology reading device supported by or incorporating such a structured finding object (SFO)-based tool is described. The radiology reading device is implemented on a server system 10, such as a network server computer, a cloud computing resource comprising ad hoc-interconnected computers, a cluster computing system, or so forth which also implements or has access to a Picture Archiving and Communication System (PACS) 12 that stores radiology images acquired by imaging devices (not shown) such as ultrasound, magnetic resonance imaging (MRI), a computed tomography (CT), positron emission tomography (PET), and/or other imaging systems, and/or by hybrid or combined imaging systems such as PET/CT imaging systems. The server 10 implements a radiology reading environment 14, which is for example the Philips iSite Enterprise radiology reading environment (available from Koninklijke Philips N.V., Eindhoven, the Netherlands). The radiologist accesses the radiology reading environment via a radiology workstation 16, which typically includes one or more display devices and/or computers connected with the server computer 10 via a wide area network (WAN), local area network (LAN), wireless local area network (WLAN), the Internet, or so forth. In addition to interfacing the radiologist with the radiology reading environment 14, the radiology workstation 16 typically also interfaces the radiologist with a radiology reporting environment 18 via which the radiologist records the radiology report, e.g. using a standardized reporting template such as an RSNA radiology reporting template. The radiology reporting environment 18 is illustrated in FIG. 1 as being incorporated into the radiology workstation 16, but may instead be implemented on the server 10 and accessed by the radiology workstation 16. Moreover, in some embodiments the radiology workstation is an integral component of the radiology reading environment, that is, a combined or integrated radiology reading and reporting environment may be provided. The radiology workstation further includes one or more user input devices 20, 22, 24 via which the radiologist may interact with the radiology reading environment 14 (for example, in order to pan or zoom images) and a display device or component 25 on which images are displayed along with graphical user interface (GUI) dialogs for user interaction, patient data, or so forth. The radiology reporting environment 18 may use the same user input devices 20, 22, 24 in order to input the radiology report as shown, or may have its own dedicated user input devices (not shown). The illustrative user input devices 20, 22, 24 include a keyboard 20, a trackpad or other pointing device 22, and a dictation microphone 24, but different, additional, or other user input devices may be provided such as a touch-sensitive display. While a single radiology workstation 16 is illustrated by way of example, it is to be understood that the radiology department of a sizable medical institution may include two, three, or more, or many radiology workstations each accessing the server-based radiology reading environment 14 and each either running its own instance of the radiology reporting environment 18 or each accessing a common server-based radiology reporting environment.

The radiology reading environment 14 includes a structured finding object (SFO) based tool or component, an illustrative example of which is diagrammatically shown in FIG. 1. The SFO-based tool provides contextually triggered automatic invocation of various third party applications (i.e. tools) via appropriate application program interface (API) components 26, and in embodiments such as the illustrative embodiment in which the radiology reporting environment 18 is separate from the radiology reading environment 14 the SFO-based tool also provides natural language text input to the radiology reporting environment 18 via an appropriate API 28. (If the radiology reporting environment is integrated with the radiology reading environment then the API 28 is not needed). The SFO-based tool also provides an SFO annotation GUI dialog displayed on (a display device of) the radiology workstation via which the radiologist can enter information supporting or characterizing the finding.

With continuing reference to FIG. 1, the radiologist invokes the SFO-based tool by selecting a radiology finding via a finding selector 30. The selector 30 can operate in various ways. In one approach, the radiologist operates an anatomy selector 32 to select an anatomical feature, image pixel or the like, in an image 33 displayed on the display component 25 of the radiology workstation 16, and the radiology finding selector 30 identifies the finding as associated with that feature or image location. The radiological finding selector 30 also retrieves an appropriate SFO template from an SFO templates database 34. By way of non-limiting illustrative example, if the radiology reading task calls for identifying a tumor in an organ, the user may indicate that this is the task being performed, and then when the user clicks on an image location using the mouse, trackpad 22, or the like the SFO-based tool selects a tumor finding object template from the SFO templates database 34. Other approaches can be used, for example the radiologist can enter a name associated with the radiological finding by typing it in via the keyboard 20 or dictating the name via the dictation microphone 24 (e.g. the name may be of the finding itself, e.g. "nodule" or "tumor" or "metastasis region" or "radial bone fracture", or more generally associated with the finding, e.g. "lung"), and the radiological finding selector 30 then identifies the radiological finding based on the entered name.

In one contemplated approach, the anatomy selector 32 is used by the radiologist to identify one or more pixels or voxels in an image as input. The radiology finding selector 30 then generates a probability distribution of predetermined anatomies. The input from the anatomy selector 32 can be derived from a two-dimensional linear measurement, e.g., by taking the measurement's start and end point pixels with or without all pixels it intersects with. In one implementation the output is a trivial probability distribution with one anatomy marked 1.0 and all others as 0.0. The probability distribution can be generated using known image segmentation techniques. The radiology finding selector 30 then retrieves the SFO template for the finding most probably associated with the identified anatomy.

The radiologist then builds an SFO representing the identified radiological finding at least in part by entering information (i.e. annotations) into the SFO template via an SFO annotation GUI dialog 40 that is displayed on the display device 25 of the radiology workstation 16. (FIG. 1 illustrates an example of the SFO annotation GUI 40 on the display 25, and also shows an enlarged representation of the SFO annotation GUI 40 in the functional diagram of FIG. 1 to illustrate its place in the processing flow). The illustrative SFO annotation GUI dialog 40 is in the form of annotation reticle 40, which is a compact design in which annotation data entry fields are represented as arc segments of the reticle 40 (or the arc segments may be selected to bring up the annotation data entry field(s) corresponding to an arc segment) for inputting various annotation values. In general, each annotation data entry field (e.g. arc segment) corresponds to a dimension represented by a <key, value> pair in the SFO (where again it is to be understood that the "value" may be a vector, array, hierarchical data structure or other complex data structure). In an optional more efficient annotation approach, upon clicking a segment (i.e. annotation data entry field) of the annotation reticle 40, previously selected elements can be presented for selection potentially ranked by frequency of occurrence in prior reports of the patient if appropriate.

The illustrative reticle design is merely an example, and other GUI dialogs can be used for building the SFO representing the identified radiological finding by annotating the retrieved SFO template that is configured to represent the radiological finding. For example, in another implementation, the SFO annotation GUI dialog is a tree structure that iteratively unfolds itself upon selection of a value for a dimension. In this implementation, each level of the tree corresponds to a dimension and the nodes in the level correspond to the dimension's values, sorted by prevalence if appropriate.

The SFO annotation GUI dialog 40 may optionally be linked to voice recognition technology so that the radiologist can interact with the SFO annotation GUI dialog 40 via the dictation microphone 24. In such an embodiment, the radiologist dictates the finding and the speech recognition populates values of dimensions of the SFO detected in the speech. For example "right upper lobe lung nodule" can populate the dimension "location" with the value "lung" and the dimension "primary diagnosis" with the value "nodule" and the dimension "sublocation" with the value "upper lobe" and the dimension "laterality" with "right".

The SFO and its annotation GUI dialog can have various additional features. For example, in some embodiments certain dimensions can be augmented with new entries manually. In some embodiments new elements can be entered from a background vocabulary, such as RadLex of SNOMED CT. In some embodiments, a dimension may have "protected" meta-data elements: for instance, the "spatial" dimension that models the finding's volume in three dimensions may have a protected meta-element "Absent" to indicate that the object of the finding (e.g. a tumor) is not observed by the radiologist in the image.

If a given SFO includes specialized annotation content, or has a large number of dimensions, this can be accommodated as additional fields in the (primary) annotation reticle 40 (e.g. with segments expanding out radially to maintain compactness), and/or by providing an additional (secondary) annotation reticle 42 having functionality similar to the first (primary) annotation reticle 40.

The SFO concept, on the one hand, and the SFO dimension concept on the other hand, provide substantial flexibility for organizing radiology findings. For example, consider a finding of lung cancer represented by an SFO whose annotations are being entered using the annotation reticle 40, in which the lung cancer SFO has a dimension of "metastasis" represented by one of the arc segments of the reticle 40. If the radiologist enters a value for the "metastasis" dimension that indicates the lung cancer has metastasized, then additional information is required to characterize the nature and extent of metastasis. In one approach, these additional information are incorporated into the lung cancer SFO as additional dimensions hierarchically "beneath" the "metastasis" dimension, and the annotations for these additional dimensions are suitably entered using radially outwardly extending segments of the original annotation reticle 40 or by bringing up a new annotation reticle, e.g. the secondary reticle 42. Alternatively, when the radiologist enters a value for the "metastasis" dimension that indicates the lung cancer has metastasized, then this might be viewed as identifying a new finding of "metastasis" and thus be fed back to the radiology finding selector 30 in order to retrieve a new SFO template for a metastasis finding. In this approach, the annotation reticle 42 is used to annotate this newly identified metastasis SFO, i.e. the annotation reticle 42 is viewed in this approach as a new primary annotation reticle for the metastasis SFO.

The SFO templates of the SFO templates database 34 are suitably created and curated by radiologists via an SFO templates configuration editor 44, which enables initial creation and subsequent editing of an SFO template, for example using a syntax such as Annotation Imaging Markup (AIM), which is a radiology domain-specific XML syntax. In general, this entails defining dimensions of the SFO template and delineating the data type and allowed value range and/or discrete set of allowed values for each dimension. Hierarchical relationships between dimensions can be set up using the hierarchical syntax of AIM, which also allows complex data types including data structures. In some embodiments, individual radiologists may be permitted to edit SFO templates. In some embodiments, the SFO templates database 34 may include personal directories or folders for individual radiologists who can edit SFO templates and save the modified SFO templates in the radiologist's personal directory or folder.

With continuing reference to FIG. 1, during SFO annotation the SFO-based tool monitors the state of the SFO by applying a set of action rules that trigger certain actions if the rule is met by the SFO being developed by the annotating. For example, the SFO-based tool may implement annotation action rules 50. When an annotation action rule is triggered, it performs an action such as displaying an annotation suggestion in a pop-up window. For example, if the radiologist enters a value for the quantitative "spatial" dimension an annotation action rule may suggest annotating the "size" dimension as "small" or "large" based on the value annotated for the "spatial" dimension. As another example, entry into the "location" dimension of "renal cortex" may trigger an action rule to suggest diagnosis="cyst" as this is a common diagnosis in this situation. This annotation action rule can be constructed using co-occurrence statistics as a conditional probability, e.g. Pr(diagnosis="cyst"|location="renal cortex"). This action rule may further use contextual data as conditional elements, e.g., Pr(diagnosis="tumor"|location="breast", sex="female"). The annotation action rules may further be configured to return frequently co-occurring combinations of annotations. This can be implemented as a presentation of annotations that contain more annotations that the input vector of annotations ranked by prevalence in a database of prior annotations. In this manner, the SFO with single annotation location ="kidney" would return ("kidney", "stable", "cyst") if stable renal cysts are the most frequent type of renal findings. Rather than suggesting the annotation associated with the satisfied annotation action rule, it is contemplated to automatically annotate the SFO with the annotation associated with the satisfied action rule. This approach may be appropriate, for example, if the action rule is essentially a tautology, e.g. if a value entered for the quantitative "spatial" dimension necessarily means the "size" dimension should be assigned the value "small", then this might be directly annotated to the SFO without first suggesting it to the radiologist and thereby obtaining the radiologist's approval.

Other action rules may be classified as quality assurance (QA) action rules 52. These action rules warn of data inconsistencies or missing data. For example, if the "spatial" dimension indicates a large tumor but the "size" dimension has the value of "small" this inconsistency can be indicated in a pop-up warning window at the time the second (inconsistent) annotation value is entered. Warnings may be similarly issued about missing data, e.g. if the "size" dimension is annotated as "small" but the "location" dimension has not been annotated a pop-up window may be displayed warning that the location should be provided. Other QA action rules may issue a warning if the value annotated for a dimension is outside of an expected range of values for the dimension (where the range in this case may be a numerical range, e.g. [lower, upper] or a set of allowed values). Some other QA action rules may include: if location="liver", specify sublocation (i.e., lobe 1 to 7); if location="lung" and diagnosis="nodule", specify spatial dimension; or if location="liver", no other sublocation can be entered other than "lobe 1", . . . , "lobe 7".

Other action rules may be classified as application program interface (API) action rules 54. These action rules detect situations in which a third party program (i.e. tool) may be usefully invoked. By "third party" it is merely meant that the third party program is a separate program from the radiology reading environment 14, such that the third party program is invoked via an API 26. The third party applications may run on the same server 10 as the radiology reading environment 14, or may run on a different server accessed via an electronic data network. The API action rules 54 provide the mechanism by which third party programs can be invoked in a context-sensitive fashion, and loaded with relevant data from the radiology reading task being performed (and, in some instances, more specifically loading the invoked application program with information from the SFO). The specific API action rules 54 are suitably chosen based on the available third party applications. By way of non-limiting illustration, the SFO-based tool of FIG. 1 includes API action rules for contextually invoking third party applications including: a medical literature viewer 160; an electronic medical record (EMR) system 162; a computer-aided diagnosis (CADx) system 164; one or more image processing applications 166; a PACS navigator 168; and electronic treatment guidelines 170. By way of further illustration, the interaction with some of these illustrative third party applications is described in the following.

The literature viewer 160 may be invoked by an API action rule that identifies particular finding characteristics which have been the subject of a recent ground-breaking medical publication. For example, the API action rule may be triggered by the combination of a particular type of tumor in a specific anatomical site with calcifications. When that action rule is triggered, the action rule utilizes the API 26 to invoke the medical literature viewer 160 loaded with a URL or other document identifier pointing to the target medical publication. This causes the medical literature viewer 160 to start up and load the target medical publication. Depending upon the features of the medical literature viewer 160 and accessibility of those features via the API 26, the medical literature viewer 160 may be further configured to highlight certain relevant passages of the target medical publication.

The EMR system 162 may be invoked by an API action rule that identifies that certain information possibly contained in the EMR may be of use. For example, demographic information such as age, ethnicity, or gender may be useful in supporting (or rejecting) a finding with certain annotations, and accordingly when those annotations are made the action rule is triggered and the EMR system 162 is invoked with a query for the demographic information of the patient (who is identified in the query based on the patient identifier that was entered into the radiology reading environment 14 at initiation of the reading task).

The CADx system 164 may be invoked by an API action rule that identifies a finding that may be supported by, or whose characteristics may be enriched by, a computer-aided diagnosis performed by the CADx system 164. For example, some CADx analyses operate directly on a radiological image by performing image pre-processing, segmentation, automatic segmentation, and automated analysis of a segmented region of the image. When the action rule detects the appropriate type of finding and type of radiological image, it invokes the CADx system 164 via the API 26 and loads it with the image and any other information needed for the CADx system 164 to perform the analysis.

Image processing applications 166 may be invoked by API action rules that detect conditions in which a particular type of image processing may be useful. For example, when assessing a tumor for calcifications it may be known that a particular type of image filtering enhances visibility of calcifications; thus, when the radiologist enters an affirmative value for the "with calcifications" dimension this automatically invokes the image filtering application loaded with the image and identification of the appropriate filter parameters for performing calcifications-enhancing filtering. Various levels of radiologist approval may be sought before doing so, for example a pop-up window may first appear stating that this filter is advantageous and asking if the radiologist wants to apply the filter—if the radiologist approves the action only then is the filter applied. In an alternative approach, if the filter is a rapidly executing filter then it may be applied and the filtered image returned to the SFO-based tool which then displays the filtered image side-by-side with the unfiltered image and requests the radiologist indicate whether the filtered image should be used.

The PACS navigator 168 may be invoked when an API action rule detects a condition for which review of past radiology examinations of the subject may be usefully compared with the current radiology examination. For example, if an action rule detects annotation of an SFO having a "temporal" dimension which assume values such as "stable", "interval increase in size", or so forth, then the rule may invoke the PACS navigator to query whether the PACS contains any comparable previous radiology examinations for the patient—if so, this is reported to the radiologist with a question as to whether the radiologist wishes to review these examinations. If the radiologist so indicates, then the radiology report(s) for these past examinations and/or their images are displayed on the radiology workstation 16 for review by the radiologist. In a contemplated more automated embodiment, an action rule may detect entry of a value for the "spatial" dimension of a tumor along with an unannotated "temporal" dimension for the tumor, and in response may invoke the PACS navigator 168 to automatically query for past examinations and parse the radiology report for the most recent past examination to extract the tumor size, compare it with the value entered into the "spatial" dimension of the SFO, and either automatically fill in the "temporal" dimension on the basis of the comparison or first present the proposed "temporal" dimension value to the radiologist for approval before updating the SFO.

In another illustrative example, the PACS navigator 168 is invoked to retrieve relevant image slices in prior examinations and present them to the radiologist for comparison based on matching the current SFO annotation with SFOs stored for prior images. In case more than one match is found, all matching slices can be presented. The matching routine can be implemented as binary subset routine: return all SFOs that have all annotations that the current annotation has and maybe more. The matching routine may optionally be implemented using fuzzy logic in which a certain portion of dimension annotations is allowed to deviate. This may especially be useful in the context of spatial dimensions, as measurements are likely to change over time.

The treatment guidelines 170 are invoked when a finding is annotated with annotations that satisfy a relevant action rule. The invoked treatment guideline 170 displays a window showing a relevant guideline, e.g. as textual document (preferably with relevant sections highlighted) or as a suggested course of action retrieved from the guideline. For instance, when an action rule detects annotating of a finding of lung cancer with a nodule size (e.g. via a "spatial" dimension) during reading of PET images, the action rule may first invoke the EMR system 162 to retrieved relevant patient data (e.g., information on smoking or other risk factors) and then invoke a Fleishner guideline application to apply the Fleishner Society Recommendations to map the measured lung nodule size along with the retrieved risk factors information to a follow-up recommendation.

As illustrated in this last example, the various action rules 50, 52, 54 may be designed to perform various sequences of actions, in so doing it will be appreciated that the illustrative delineation of annotation, QA, and API rules is not rigid. For example, an action rule may invoke a third party application to generate or retrieve data (an API action rule) and the data then compared with existing annotations of an SFO to assess consistency (a QA action rule) and then update a dimension value (an annotation action rule). Action rules may also be triggered by information generated by previous API calls to third party applications. More generally, action rules can leverage various types of contextual information, such as content of the radiology examination being read (e.g. the imaging modality, the examination protocol, or so forth), information about the radiologist (for example, an action rule for invoking the medical literature viewer 160 may take into account the expertise of the radiologist so as to avoid presenting literature to a radiologist already highly knowledgeable in the relevant area), clinical context (e.g. patient information provided to the radiology reading environment 14 during the reading or retrieved from the EMR system 162), the current state of the SFO, the existence of other SFOs characterizing related findings already made by the radiologist, information generated by API calls to third party applications, or so forth.

With continuing reference to FIG. 1, a third party information presenter 56 is provided to present information obtained from invoked third party applications to the radiologist in a form that effectively melds with the radiology reading environment 14. The information presentation engine 56 may have one or more presentation templates into which diverse output types are fitted, so as to enforce homogeneity of the user interface. The presentation templates may provide for controlled user interactions such as clicking or hovering over a presented element. Semantics of the interactions can be defined on a case-by-case basis. The third party information presenter 56 may optionally present information using the same format as the SFO annotation GUI dialog 40, e.g. as additional data entry fields represented similarly to SFO dimensions (as arc segments in the illustrative case of the annotation reticle dialog).

The informational output of the SFO-based tool for a given finding includes a completed (i.e. built) SFO 60 and any additional information generated by third party applications which is presented to the radiologist via the information presenter 56 and approved by the radiologist for inclusion in the radiology report. The completed SFO 60 contains information including the finding (generally defined by the SFO template which was annotated to produce the completed SFO 60) and the annotations to the SFO template which provide information supporting or characterizing the finding. Information generated by third party applications is formatted by the third-party information presenter 56, and hence is also in some structured format.

On the other hand, the radiology report which the radiologist prepares using the radiology reporting environment 18 is typically less structured. The radiology report may be prepared by the radiologist using a standardized reporting template such as an RSNA radiology reporting template, but such templates generally include freeform text fields into which the radiologist enters findings in an unstructured manner.

To bridge the gap between the structured format of the completed SFO 60 (and any third party application information structured by the information presenter 56) and the freeform textual format of the radiology report, the illustrative SFO-based tool further includes a natural language generation (NLG) component 62 which generates natural language text content expressing the information of the completed SFO 60 and any third party application information in a format suitable for inclusion in the radiology report. In one embodiment, the NLG component 62 concatenates non-empty values with appropriate labels assigned to the dimensions where needed for readability, for example "non-enhancing kidney lesion" or "1×1.1 cm lobe 3 liver tumor". In more complex implementations, certain information may be condensed using rules, or employing natural language templates with fields that are filled in with dimension values of the completed SFO 60. For example, such a natural language template in the English language might be: "A <structure> is observed in the <sub-location> of the <organ>." The NLG component 62 would fill in the <structure> field with an English-language label for the structure identified in the completed SFO 60 (for example, filling in <structure> with "tumor" or "nodule" or "lesion" as appropriate). The NLG component 62 would fill in the <organ> field with an English-language label for the organ in which the tumor et cetera was observed, e.g. the <organ> field might be filled in with "liver" or "kidney" or so forth, where this is obtained from the "anatomy" dimension of the SFO. Likewise, the NLG component 62 would fill in the <sub-location> field with the appropriate structure identified by the value of the "sub-location" dimension of the completed SFO 60. In some embodiments, the NLG component 62 may employ still more complex processing to generate the natural language text, such as utilizing a grammatical parser or so forth.

The textual output of the NLG component 62 is formatted for inclusion in a radiology report, and is provided to the radiology reporting environment 18 via a suitable API 28 designed to interface with the particular radiology reporting environment 18 being used by the radiologist. In one embodiment, the integration of the natural language content from the NLG component 62 is mediated by the radiologist. For example, the API 28 may copy the natural language content into a clipboard which is also accessible from the radiology reporting environment 18, so that the radiologist can paste the content into the radiology report via a user operation such as the combination of keystrokes ("CTRL+ V") which is commonly used for paste operations in word processing or text editor user interfaces. In a more sophisticated embodiment of the API 28, the natural language content is automatically copied into the appropriate section of the radiology report, optionally highlighted so that the radiologist is encouraged to review it before finalizing and filing the report. It should be noted that in some embodiments the API 28 may be omitted entirely. For example, the NLG component 62 can display the generated natural language content in a window of the SFO-based tool, and the radiologist is then required to use system-level cut-and-paste or copy-and-paste operations to transfer it into the radiology report. For example, if the radiology workstation 16 employs conventional Windows or MacOs user interfacing systems, the text can be cut or copied from the window using CTRL-X or CTRL-C, respectively, and can be pasted into the radiology report using CTRL-V.

Further, if the radiology reporting environment is integrated with the radiology reading environment, then the API 28 is suitably replaced by an equivalent processing block of the combined reading/reporting environment that transfers the natural language text generated by the NLG component 62 into the radiology report.

Figure 2:
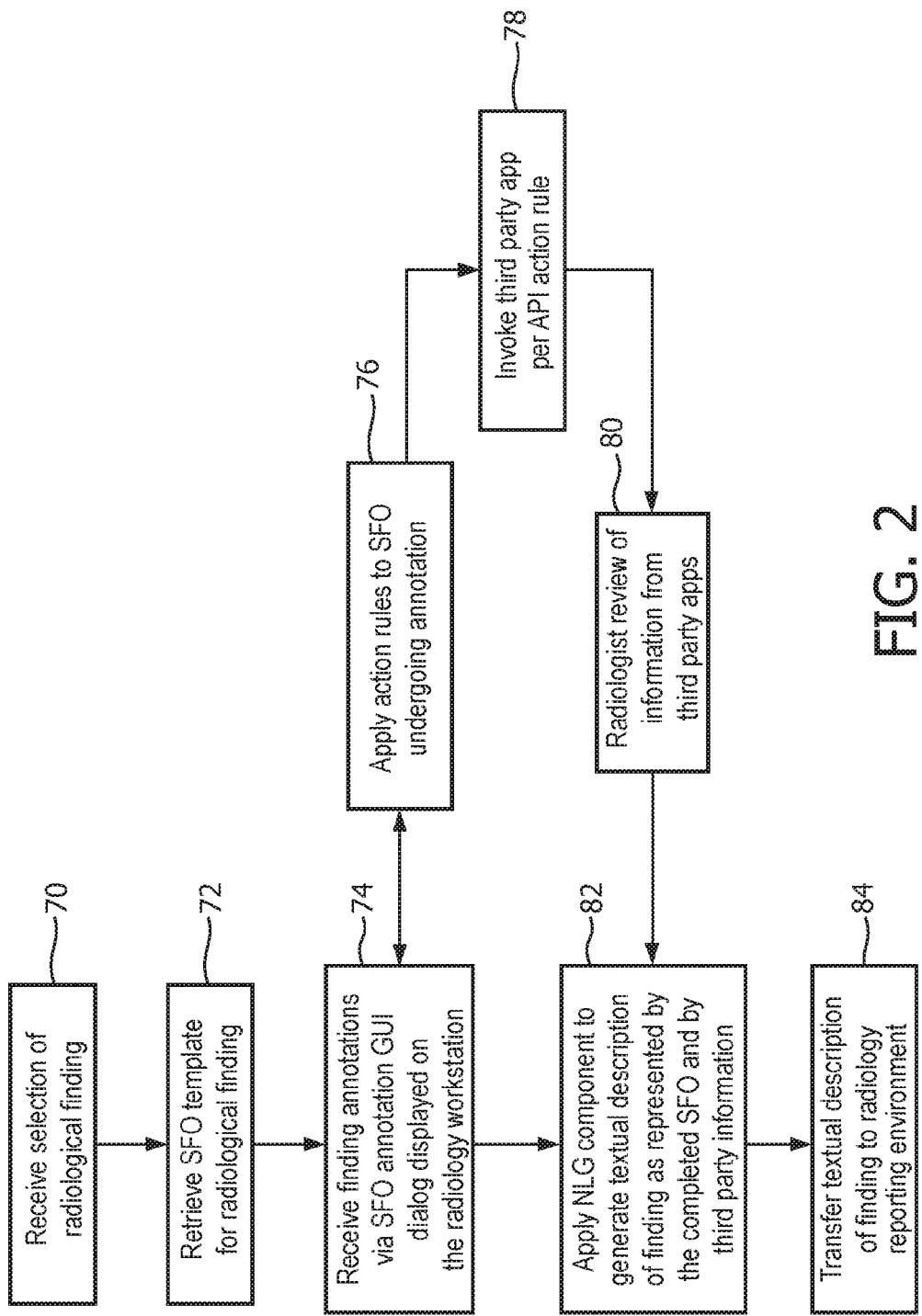
FIG. 2 diagrammatically illustrates a radiology reading task work flow suitably performed using the radiology reading device of FIG. 1.

With reference now to FIG. 2, an illustrative process using the SFO-based tool in performing a radiology reading using the system of FIG. 1 is described. In an operation 70, a radiology finding is selected using the finding selector 30, e.g. employing the anatomy selector 32 or detecting a dictated finding. In an operation 72, the SFO template for the selected finding is retrieved from the SFO templates database 34. In an operation 74, the SFO-based tool receives annotations supporting or characterizing the selected radiological finding via the SFO annotation GUI dialog 40. During this annotating 74, in an operation 76 the action rules 50, 52, 54 are applied to the SFO undergoing annotation to determine whether the developing SFO satisfies any action rule. If an action rule is met at some point during the annotation process 74, then an appropriate action is taken, such as an illustrative operation 78 in which a third party application is invoked in accordance with a triggered API action rule (e.g. one of the illustrative third party applications 160, 162, 164, 166, 168, 170 of FIG. 1, or an ordered sequence of such applications). If a third party application or applications are invoked, then in an operation 80 the information generated by the third party application is formatted by the information presenter 56 for review by the radiologist. When the annotating 74 is complete, a NLG operation 82 is performed in which the NLG component 62 formats informational content of the completed SFO, along with any other information generated from the third party applications (and optionally filtered by approval of the radiologist) into natural language text which is transferred to the radiology report in an operation 84.

It will be appreciated that the illustrative computational, data processing or data interfacing components of the SFO-based tool, e.g. components 26, 28, 30, 32, 56, 62 may be embodied as a non-transitory storage medium storing instructions executable by an electronic processor (e.g. the server 10) to perform the disclosed operations. The non-transitory storage medium may, for example, comprise a hard disk drive, RAID, or other magnetic storage medium; a solid state drive, flash drive, electronically erasable read-only memory (EEROM) or other electronic memory; an optical disk or other optical storage; various combinations thereof or so forth.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A radiology reading device comprising:
a server computer programmed to operate with a radiology workstation to perform a radiology reading task including performing an SFO-based radiology reading support method including:
receiving user input identifying a radiological finding via at least one user input device of the radiology workstation;
retrieving from a data storage a structured finding object (SFO) template comprising a structured data object configured to represent the identified radiological finding;
displaying an SFO annotation graphical user interface (GUI) dialog on a display device of the radiology workstation, the SFO GUI dialog having annotation data entry fields for annotating the retrieved SFO template;
building an SFO representing the identified radiological finding by annotating the retrieved SFO template at least in part with information received via the at least one user input device interacting with the SFO GUI dialog displayed on the display device of the radiology workstation;
generating natural language text describing the identified radiological finding from the SFO representing the identified radiological finding; and
transferring the natural language text describing the identified radiological finding to a radiology report under draft in a radiology reporting task operating with the radiology workstation.

2. The radiology reading device of claim 1 wherein:
the SFO template is configured to represent the identified radiological finding at least by defining <key, value> pairs in which the key denotes a dimension of the SFO representing information supporting or characterizing the identified radiological finding and the value denotes a value for the dimension;
the SFO GUI dialog has annotation data entry fields for entering values for dimensions of the retrieved SFO template; and
the SFO representing the identified radiological finding is built at least in part by receiving values for dimensions of the retrieved SFO template using the at least one user input device interacting with the displayed SFO GUI dialog.

3. The radiology reading device of claim 2 wherein the SFO templates are structured Annotation Imaging Mark-up (AIM) objects employing XML syntax.

4. The radiology reading device of claim 2 wherein each SFO template defines <key, value> pairs in which the value is configured to assume values only from a set of possible values chosen from a radiology ontology.

5. The radiology reading device of claim 2 wherein the operation of generating natural language text includes: generating natural language text by filling in one or more fields of a natural language template with values of dimensions of the SFO.

6. The radiology reading device of claim 1 wherein the SFO-based radiology reading support method further includes:

during the building of the SFO representing the identified radiological finding, applying annotation action rules to the SFO to determine whether the SFO satisfies any annotation action rule; and in response to determining an annotation action rule is satisfied, one of (i) displaying an annotation associated with the satisfied annotation action rule and (ii) annotating the retrieved SFO template with the annotation associated with the satisfied annotation action rule.

7. The radiology reading device of claim 1 wherein the SFO-based radiology reading support method further includes:

during the building of the SFO representing the identified radiological finding, detecting a missing or inconsistent or out-of-range annotation of the SFO using a quality assurance (QA) action rule; and in response to the detecting, displaying a warning of the detected missing or inconsistent or out-of-range annotation of the SFO.

8. The radiology reading device of claim 1 wherein the SFO-based radiology reading support method further includes:

during the building of the SFO representing the identified radiological finding, applying application program interface (API) action rules to the SFO to determine whether the SFO satisfies any API action rule; and in response to an API action rule being satisfied by the SFO, invoking an application program corresponding to the satisfied API action rule.

9. The radiology reading device of claim 8 wherein the invoking of the application program corresponding to the satisfied API action rule includes loading the invoked application program with data from the radiology reading task.

10. The radiology reading device of claim 8 wherein the API action rules include API action rules for invoking application programs selected from the group consisting of: a medical literature viewer, an electronic medical record system, a computer-assisted diagnosis system, an image processing application, a Picture Archiving and Communication System (PACS) navigator, and an electronic treatment guideline.

11. The radiology reading device of claim 8 wherein the SFO-based radiology reading support method further includes:

receiving information from the invoked application program via an application program interface (API); and displaying the information received via the API using a presentation engine that presents information received from different application programs in a common format.

12. The radiology reading device of claim 1 wherein the operation of receiving user input identifying a radiological finding includes receiving identification of an image location in a radiological image being read, determining anatomy associated with the identified image location, and identifying the radiological finding based on the anatomy.

13. The radiology reading device of claim 1 wherein the operation of receiving user input identifying a radiological finding includes receiving a name associated with the radiological finding typed on a keyboard or dictated via a dictation microphone and identifying the radiological finding based on the received name associated with the radiological.

14. The radiology reading device of claim 1 wherein the displayed SFO annotation GUI dialog comprises an annotation reticle in which annotation data entry fields are represented by arc segments of the annotation reticle.

15. A radiology reading system comprising:

a data storage storing structured finding object (SFO) templates, each SFO template being a structured data object configured to represent a radiological finding;

a radiology workstation including a display device and at least one user input device; and a radiology reading device comprising a server computer as set forth in claim 1 programmed to operate with the radiology workstation to perform the radiology reading task including performing the SFO-based radiology reading support method.

16. A non-transitory storage medium storing instructions readable and executable by an electronic device to perform a radiology reading support method in support of a radiology reading task also being performed on the electronic device operating with a radiology workstation, the radiology reading support method comprising:

receiving user input identifying a radiological finding via at least one user input device of the radiology workstation;

retrieving from a data storage a structured finding object (SFO) template configured to represent the identified radiological finding at least by defining <key, value> pairs in which the key denotes a dimension of the SFO representing information supporting or characterizing the radiological finding and the value denotes a value for the dimension;

displaying an SFO annotation graphical user interface (GUI) dialog on a display device of the radiology workstation, the SFO GUI dialog having annotation data entry fields for entering values for dimensions of the SFO template;

building an SFO representing the identified radiological finding at least in part by receiving values for dimensions of the SFO template using the at least one user input device of the radiology workstation interacting with the displayed SFO GUI dialog; and generating natural language text describing the identified radiological finding from the SFO representing the identified radiological finding.

17. The non-transitory storage medium of claim 16 wherein the SFO-based radiology reading support method further comprises:

during the building of the SFO representing the identified radiological finding, applying action rules to the SFO to determine whether the values of the dimensions of the SFO satisfy any action rule; and in response to determining an action rule is satisfied, performing an annotation, quality assurance, or application program interfacing action associated with the satisfied action rule.

18. The non-transitory storage medium of claim 16 wherein the SFO-based radiology reading support method further includes:

during the building of the SFO representing the identified radiological finding, applying application program interface (API) action rules to the SFO to determine whether the SFO satisfies any API action rule; and in response to an API action rule being satisfied by the SFO, invoking an application program corresponding to the satisfied API action rule with the invoked application program loaded with data from the radiology reading task.

19. The non-transitory storage medium of claim 16 wherein the operation of receiving user input identifying a radiological finding includes one of:

receiving identification of an image location in a radiological image being read, determining anatomy associated with the identified image location, and identifying the radiological finding based on the anatomy; and receiving a name associated with the radiological finding typed on a keyboard or dictated via a dictation microphone and identifying the radiological finding based on the received name associated with the radiological.

20. The non-transitory storage medium of claim 16 wherein the SFO-based radiology reading support method further comprises:

transferring the natural language text describing the identified radiological finding to a radiology report under draft in a radiology reporting task operating with the radiology workstation.

* * * * *